United States Patent
Günther

(10) Patent No.: US 8,187,568 B2
(45) Date of Patent: May 29, 2012

(54) METHOD AND PLANT FOR THE PRODUCTION OF SYNTHESIS GAS FROM BIOGAS

(75) Inventor: Lothar Günther, Geretsried (DE)

(73) Assignee: DGE Dr. Ing. Guenther Engineering GmbH, Wittenberg (DE)

( * ) Notice: Subject to any disclaimer, the term of this patent is extended or adjusted under 35 U.S.C. 154(b) by 68 days.

(21) Appl. No.: 12/673,239

(22) PCT Filed: Aug. 12, 2008

(86) PCT No.: PCT/EP2008/006614
§ 371 (c)(1), (2), (4) Date: Feb. 12, 2010

(87) PCT Pub. No.: WO2009/021710
PCT Pub. Date: Feb. 19, 2009

(65) Prior Publication Data
US 2011/0175032 A1    Jul. 21, 2011

(30) Foreign Application Priority Data
Aug. 16, 2007 (DE) .......... 10 2007 038 760

(51) Int. Cl.
*C01B 3/24* (2006.01)
*C01B 3/38* (2006.01)
(52) U.S. Cl. .......... 423/650; 252/373
(58) Field of Classification Search ........ 423/650–654
See application file for complete search history.

(56) References Cited

U.S. PATENT DOCUMENTS
| | | | |
|---|---|---|---|
| 5,714,092 A * | 2/1998 | van Looij et al. | 252/373 |
| 6,299,994 B1 * | 10/2001 | Towler et al. | 429/412 |
| 7,427,388 B2 * | 9/2008 | Garg et al. | 423/653 |
| 2004/0023086 A1 * | 2/2004 | Su et al. | 429/17 |
| 2004/0180247 A1 * | 9/2004 | Higashiyama et al. | 429/19 |
| 2005/0013754 A1 * | 1/2005 | Kobayashi et al. | 422/198 |

FOREIGN PATENT DOCUMENTS
| | | |
|---|---|---|
| DE | 4322738 A1 | 1/1995 |
| DE | 20202722 U1 | 5/2002 |
| DE | 60116602 T2 | 11/2006 |
| DE | 102005031224 A1 | 1/2007 |
| EP | 1604727 A1 | 12/2005 |

OTHER PUBLICATIONS
Zimmermann: "Investigations Into the Use of Oxidation Catalysts Fitted to Agricultural Biogas Internal Combustion Engines", Oct. 6, 2003, p. 47. English abstract.

* cited by examiner

*Primary Examiner* — Melvin Mayes
*Assistant Examiner* — Kenneth Vaden
(74) *Attorney, Agent, or Firm* — Laurence A. Greenberg; Werner H. Stemer; Ralph E. Locher

(57) ABSTRACT

A method and system produce a synthesis gas from a biogas. The method provides a more economic process control and a higher yield. For this purpose hydrogen sulfide and carbon dioxide of the biogas are nearly completely separated in separate cleaning steps before a catalytic conversion of the biogas, wherein hydrogen sulfide is biologically removed by the admixture of oxygen and/or oxidation agents containing oxygen. The oxygen, or the oxidation agent, is dosed such that an excess of oxygen of at least 1.0 vol.-% is present in the cleaned biogas (methane gas). The biogas is concentrated without any dehumidification, heated, and mixed with superheated steam. Due to the excess of oxygen, thermal energy is additionally created during the reforming process by an exothermal oxidation of oxygen contained in the biogas together with hydrogen in the catalyst bed for the endothermal conversion of methane to the synthesis gas.

15 Claims, 1 Drawing Sheet

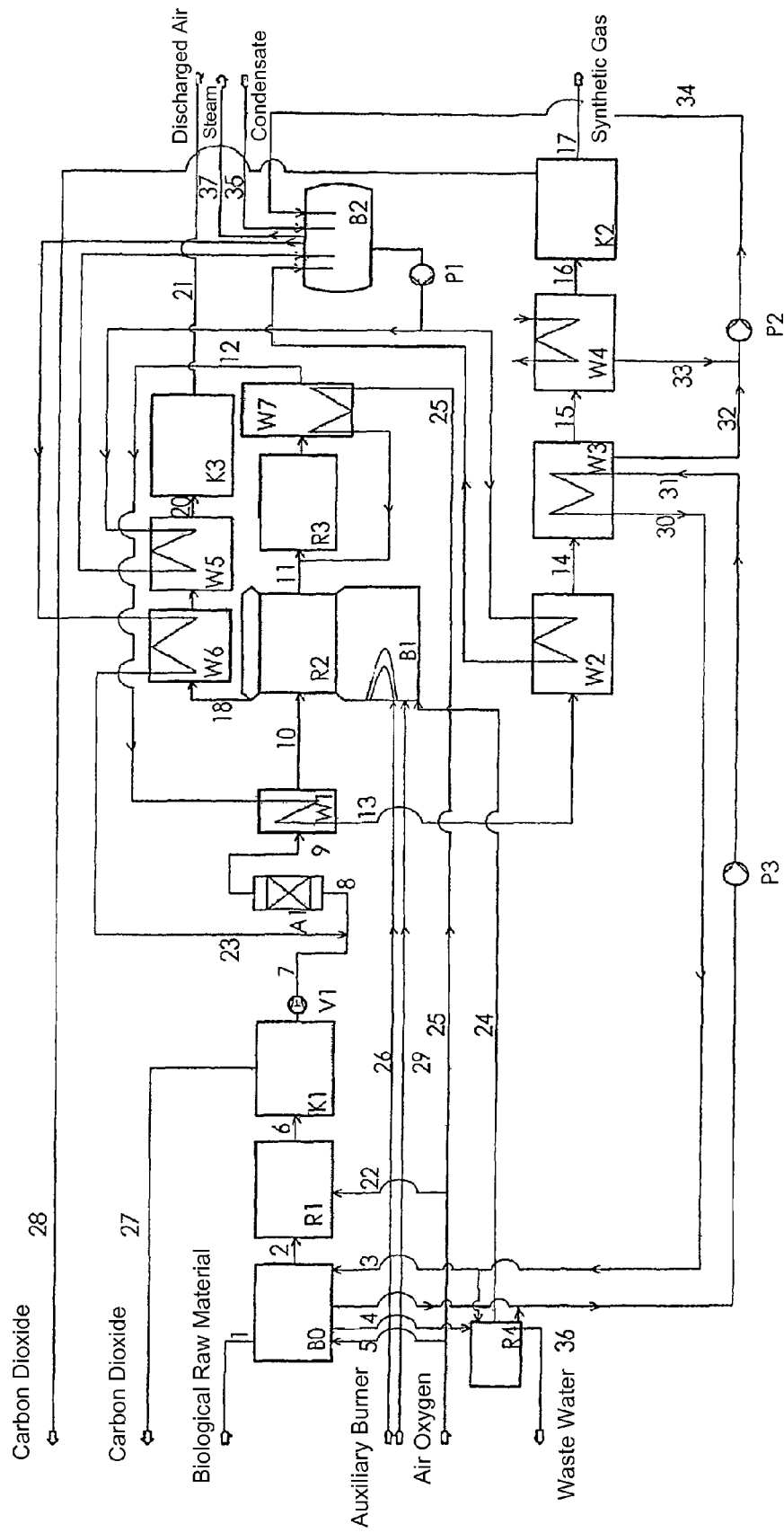

METHOD AND PLANT FOR THE PRODUCTION OF SYNTHESIS GAS FROM BIOGAS

BACKGROUND OF THE INVENTION

Field of the Invention

The invention relates to a method of producing synthesis gas from biogas, and a suitable plant for carrying out the method. Synthesis gas can be converted catalytically in a manner known per se into higher hydrocarbons, especially liquid fuels for internal combustion engines.

BRIEF SUMMARY OF THE INVENTION

Biogas is formed by the anaerobic (oxygen-free) fermentation of organic material and is used as a renewable energy source. The gases produced are classified as sewage gas, landfill gas and biogas, depending on the raw materials used, which comprise raw materials containing biomass, farmyard manure such as slurry and dung and renewable raw materials.

The term "biogas" used in this description and the claims is to be taken to mean all gases formed by fermentation. The afore-mentioned gases also contain carbon dioxide and hydrogen sulfide as well as small residual amounts of other chemical substances.

A method is known from DE 31 30 013 A1 of liquefying biogas in which the unseparated constituents of biogas, i.e. methane, carbon dioxide and water, are converted endothermically to synthesis gas via a catalyst at a carbon monoxide/hydrogen ratio between 1:1 to 1:3 with water being added if required. The synthesis gas is subsequently converted to liquid hydrocarbons by catalytic hydration. A method and device for producing methanol from biogas is described in DE 198 27 154 C2 in which biogas is converted to synthesis gas thermo-catalytically and thermo-neutrally in a reformer in the presence of a circulating catalyst without the addition of steam. In this process the biogas is converted catalytically to synthesis gas in a two-stage reforming process under increased pressure and temperature, with $CO_2$ being removed from said synthesis gas by physical scrubbing. The scrubbing solution is relaxed and re-emits at the outlet the desorbed constituents of $CO_2$ and $H_2S$ which are burned together with air and released to the surroundings. The pure synthesis gas is subsequently catalytically converted to methanol. The circulating catalyst is regenerated in a downstream combustion stage by oxidizing the carbon deposited in the reformer.

A further alternative use for biogas plants is known (DE 10 2005 031 224 A1) in which the methane which has been extracted is processed to form pure methane and converted to methanol in a cracking plant. Further details of how the gas liquefaction was carried out are not given in this publication.

The known methods are very expensive in terms of energy input and equipment required, since biogas contains approximately 2 to 2.5 times as much $CO_2$ as methane. In addition, the hydrogen sulfide in the biogas has a negative effect on the catalytic conversion and reduces the yield of synthesis gas, which is further reduced by the $CO_2$ present. Hydrogen sulfide and organic sulfur compounds act as catalyst poisons.

Furthermore, hydrogen sulfide is extremely corrosive so that the plants used for producing synthesis gas have to meet special requirements.

Hydrogen is lost in a thermo-catalytic and thermo-neutral conversion of biogas to synthesis gas, resulting in a reduction in the volumes of synthesis gas produced.

The aim of the invention is to devise a method for producing synthesis gas from biogas which employs a more efficient process control and produces a higher yield. In addition, a plant suitable for carrying out the method is to be devised.

The above aim is solved in accordance with the invention.

Before biogas is catalytically converted to synthesis gas, hydrogen sulfide and carbon dioxide are almost completely removed from it in separate scrubbing stages.

Hydrogen sulfide is biologically removed by adding oxygen and/or an oxidizing agent containing oxygen, with the oxygen or oxidizing agent so dosed that there is excess oxygen of at least 1.0% by volume in the purified biogas (methane).

Advantageously, the purified biogas does not require dehumidifying. It is subsequently compressed, heated and mixed with superheated steam. Thermal energy is therefore additionally created during the reforming process by means of an exothermic oxidation of the oxygen in the biogas with hydrogen to initiate the reaction quickly in the catalyst bed for the endothermic conversion of the methane to synthesis gas. This method offers great advantages in terms of the economical operation of the process because the reforming process is initiated by the intrinsic temperature rise of the biogas, dispensing with the need for external energy supplies and reducing the amount of catalyst required.

About 80 to 90% of the hydrogen sulfide contained in the biogas can be removed as early as at the fermenter stage, using additives, such as iron salts or by adding pure oxygen or an oxidizing agent containing oxygen. The residual content of hydrogen sulfide, based on a biogas with a sulfur content of 700 to 1500 ppm, then amounts to approximately 70 to 300 ppm. This can be almost completely removed down to 10 to 50 ppm by the further addition of oxygen in a downstream biological desulfurization process.

Hydrogen sulfide can also be removed solely in a downstream biological desulfurization process. In this case, however, the total amount of oxygen required including the required excess oxygen must be fed in.

The biogas containing hydrogen sulfide produced in the biogas plant can also be stored temporarily and the required quantity of oxygen added.

$H_2O_2$ or NaOCl, for example, can be used as oxidizing agents containing oxygen. The desulfurization of biogas is a complicated process since various overlapping reactions take place:

$$2H_2S + O_2 \rightarrow 2S + 2H_2O$$

$$2H_2S + 3O_2 \rightarrow 2H_2SO_3$$

$$H_2S + 2O_2 \rightarrow H_2SO_4$$

Accordingly, the required quantity of oxygen should be distributed as evenly as possible to the fermenter and the downstream biological desulfurization unit.

The total quantity of oxygen to be fed in should be at least 8.5 mol $O_2$/mol $H_2S$ in order to ensure the required excess oxygen is present.

It is advantageous for the subsequent reforming process if the purified biogas still contains at least 0.05% hydrogen by volume.

In accordance with the method, the excess oxygen in the purified biogas should be continuously measured or measured at specific intervals as a control variable for the feeding-in of water and external thermal energy for the reforming process.

The $CO_2$ contained in the biogas and the small residual amounts of hydrogen sulfide are removed by physical or chemical scrubbing with a scrubbing solution containing an amine. The hydrogen sulfide content can therefore be reduced down to a few hundredths of a ppm. Superheated steam, formed from the condensate accumulating in the waste heat recovery stages, is added to the purified biogas after compression. In addition, all constituents of organic sulfur should be completely removed before the introduction of the biogas into the reformer in order to prevent damage to the catalyst.

The reforming process should preferably be carried out as a two-stage process. The purified biogas (methane) is firstly compressed to a pressure of 10 to 50 bar, heated to a temperature of approximately 600 to 80° C. and subsequently mixed with the required residual quantity of oxygen and/or water or saturated steam. Conversion to approximately at least 90% by volume of synthesis gas subsequently takes place at reaction temperatures of 800 to 900° C. in an initial reforming stage in which a part of the required thermal energy is produced by reaction of the excess oxygen contained in the methane. Further conversion to over 99.5% by volume of synthesis gas takes place in the subsequent second reforming stage with oxygen fed in at reaction temperatures of approximately 1000° C.

The oxygen gas to be fed in is heated in a heat exchanger and added to the synthesis gas immediately before entry into the secondary reformer. The gas containing oxygen can be provided by means of a pressure swing adsorption plant. Most of the thermal energy required for the high reaction temperatures during the reforming stages can be provided without the need for energy from external sources.

The synthesis gas produced in the second reforming stage is therefore used for the indirect heating of the methane. After being dried, the fermentation substrate accumulated in the biogas plant is used as a fuel for producing reaction heat for the first reforming stage, enabling biogas to be converted into synthesis gas extremely economically. Waste intended for incineration systems, e.g. domestic waste, can also be used as a fuel instead of the fermentation substrate.

The carbon dioxide is subsequently removed from the synthesis gas exiting the secondary reformer, said process being carried out in a scrubbing column by means of a scrubbing solution containing an amine.

The $CO_2$-free synthesis gas can subsequently be used in a manner known per se for synthesizing liquid fuels, methanol, and ammonia or for separation into hydrogen and carbon monoxide. The respective scrubbing solutions from the biogas and synthesis gas scrubbing are preferably fed into a common scrubbing solution regeneration device. The purified scrubbing solution is re-circulated.

A plant suitable for carrying out the method comprises a biogas plant with at least one fermenter, a plant for processing and drying the fermentation substrate accumulating in the biogas plant, a biological desulfurization device downstream of the biogas plant and an initial scrubbing column downstream of that for removing carbon dioxide, a compressor for compressing the methane to synthesis gas pressure, an initial heat exchanger for heating the compressed methane to temperatures above 500° C., a reformer unit for the catalytic conversion of methane to synthesis gas, at least one unit for recovering waste heat from synthesis gas and/or waste gas, a second scrubbing column for removing carbon dioxide from synthesis gas and a feeder for oxygen or an oxidizing agent.

The reformer unit preferably comprises a primary reformer and a downstream secondary reformer. The feeder for oxygen or an oxidizing agent is connected via an initial line to a second heat exchanger for heating the gas containing oxygen to synthesis gas temperature, said line being integrated into the line for feeding synthesis gas into the secondary reformer.

The secondary reformer is connected to an output line which runs through a heat exchanger as a heat exchanger coil, which is downstream of the primary reformer and is intended for heating the methane. The line carrying the synthesis gas is connected downstream of the first heat exchanger via a line to an additional (third) heat exchanger for producing steam. This heat exchanger is connected via a further line to a fourth heat exchanger for producing hot water. An additional synthesis gas line branching off from this is connected to a fifth heat exchanger for producing how water or steam in. The synthesis gas passes into the second scrubbing column via an additional line. A supply and return line carrying hot water is integrated into the fourth heat exchanger, said line being connected to the biogas plant and the fermentation substrate processing plant to provide hot water for heating purposes. The primary reformer is connected to a line leading off waste gas which is connected to a heat exchanger unit formed as a steam superheater.

The plant is equipped with a steam drum connected to the heat exchangers intended for generating steam and hot water, with said drum receiving the condensate and steam returned from the heat exchangers and passing on the excess steam stored temporarily.

The biogas plant and the desulfurization unit are connected to lines for feeding in oxygen or an oxidizing agent.

The third heat exchanger and the fifth heat exchanger are equipped with a common superheater stage.

An adsorber arranged downstream of the first scrubbing column can be provided for fine desulfurization of the biogas.

Excess steam no longer required within the plant can be fed to a steam turbine for generating electricity.

BRIEF DESCRIPTION OF THE DRAWING

The single FIGURE of the drawing is an illustration of a plant for producing synthesis gas from biogas according to the invention.

The invention will now be explained by means of the following execution example. The functional diagram in the associated drawing depicts a plant for producing synthesis gas from biogas in conjunction with a biogas plant.

DESCRIPTION OF THE INVENTION

Biogas is produced in a biogas plant BO with 20 fermenters and 10 post fermenters, using maize silage as a fermentation substrate. 45.5 t/h of maize silage are required to produce 10,000 $Nm^3/h$ biogas, corresponding to 350 $m^3/h$ of slops. The maize silage as a biological raw material is fed via a suitable feeder 1 into the individual fermenters which are heated (to approximately 80° C.) by the hot water fed in via the line 3. This hot water can also be obtained as a return flow from the fermentation substrate R4. The damp fermentation substrate 4 accumulating in the biogas plant BO is dried in a processing unit R4 and the waste water accumulating in the process is led off via a line 36, said waste water being returned to the fermenters for a further mashing process.

After treatment by centrifuge in the processing unit R4, the fermentation substrate 4 is dried by steam or hot water. Steam is generated in the steam generators W2 and W5 and fed in via the line 37. Hot water is produced in the heat exchanger W3 and fed in and led off via the supply and return lines 30 and 31.

The operating mode of the fermenters for producing biogas is controlled in such a way as to produce biogas with as small a content of hydrogen sulfide as possible. Pure oxygen is introduced into the fermenters via the line 5 to carry out primary desulfurization and is so dosed as to produce in the biogas a concentration of oxygen of 0.2% by volume as excess oxygen.

Under these conditions 80 to 90% of the hydrogen sulfide contained in the biogas can be removed in the fermenters. The amount of hydrogen sulfide of approximately 1500 ppm contained in the biogas is thus reduced to 70 to 300 ppm. The biogas 2 produced is fed to a downstream biological desulfurization unit R1 in which the proportion of hydrogen sulfide is reduced to a value of 10 to 50 ppm by the further addition of oxygen via the line 22.

In this example approximately 31 $Nm^3/h$ of pure oxygen are required in theory to remove 1500 ppm of hydrogen sulfide from 10,000 $Nm^3/h$ biogas. It is advantageous to distribute this amount of oxygen as evenly as possible to the fermenters and to the downstream biological desulfurization unit as well and to operate the process with a required excess oxygen of approximately 100 $Nm^3/h$.

After removal of $H_2S$ in the desulfurization unit R1 the biogas produced 6 has the following composition:

| | |
|---|---|
| $CH_4$ | 51% by volume |
| $H_2$ | 0.1% by volume |
| $H_2O$ | 3.1 by volume |
| $CO_2$ | 41.9 by volume |
| $N_2$ | 0.2 by volume |
| $O_2$ | 1.0 by volume |
| $H_2S$ | 17.5 ppm |

The desulfurized biogas 6 is subsequently fed to a scrubbing column K1 in which the scrubbing process for removing the $CO_2$, the residual $H_2S$ and COS (organic sulfur compounds) is carried out under standard pressure or low vacuum (−10 to 150 mbar), using a scrubbing solution containing an amine. This solution has an amine concentration of 15 to 70%, preferably 50%, with diethanolamine being used as the amine. $CO_2$ and the other, afore-mentioned compounds are chemically bound in the scrubbing solution in a scrubbing column with a packed bed by means of the scrubbing process carried out under the counter flow principle. The said solution is subsequently regeneratively processed in a separate plant to enable the scrubbing solution to be circulated in the circuit. The carbon dioxide removed is led off via the line 27 for further utilization. 5.8 MW of heat output in the form of steam is required for the regeneration of the scrubbing solutions accumulating in the columns K1 and K2. This steam is produced in the steam generator W2 from waste heat from the synthesis gas and in the steam generator W4 from waste heat from the waste gases from the combustion of the fermentation substrate in the first reforming stage.

After removal of $CO_2$ (scrubbing column K1) the purified biogas (amounting to 5360 $Nm^3/h$) led off via the line 7 has the following composition:

| | |
|---|---|
| $CH_4$ | 95.15% by volume |
| $H_2$ | 0.19% by volume |
| $H_2O$ | 2.05 by volume |
| $CO_2$ | 0.37 by volume |
| $N_2$ | 0.37 by volume |
| $O_2$ | 1.87 by volume |
| $H_2S$ | 0.01 ppm |

After removal of the $CO_2$ the purified methane should still contain at least 1.0% of oxygen by volume as excess oxygen to enable the reforming process to be initiated by intrinsic temperature rise. It is advantageous if the biogas still contains hydrogen (e.g. 0.2% by volume). 1.8% by volume of excess oxygen thus corresponds to 8.5 mol $O_2$/mol $H_2S$, based on the biogas containing hydrogen with a sulfur content of approximately 1500 ppm.

Advantageously, the purified biogas does not require dehumidifying for further treatment of the purified biogas and can be fed directly to the compressor V1. A further advantage of the method is that the compressed gas is not cooled and the heat of compression is used simultaneously for heating the biomethane to the synthesis gas temperature. Although synthesis gas can also be produced under standard pressure, the biomethane in this example is compressed to a pressure of 15 bar (energy consumption approximately 480 kW). In this process the biomethane is not cooled in the final compressor stage and is mixed in the line 7 with superheated steam heated to 450° C. at 20 bar at a temperature of 150° C. and decompressed to a pressure of 15 bar. The superheated steam required for this is produced in the heat exchanger unit W6, W5 and fed in via the line 23. In this process 13,650 kg/h of superheated steam and 2.5 kg/$Nm^3$ biomethane or methane are mixed at a mixing temperature of the biomethane/steam mixture of approximately of 350° C. in the line 8.

The biomethane/steam mixture 8 undergoes fine desulfurization in the downstream adsorber A1, using the hydrogen contained in the biomethane. The organic sulfur, such as thiophene, is removed in this process in accordance with the following reaction:

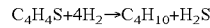

$$C_4H_4S + 4H_2 \rightarrow C_4H_{10} + H_2S$$

Under the conditions obtaining the organic sulfur compounds decompose to form $C_4H_{10}$ and hydrogen sulfide. The organic sulfur is present only in traces with few ppm. It acts, however, as a catalyst poison and should therefore be removed. The hydrogen sulfide formed as a result is completely bound in the adsorber A1 by adsorption to zinc oxide:

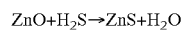

$$ZnO + H_2S \rightarrow ZnS + H_2O$$

The adsorption agent loaded with zinc sulfide is disposed of separately.

The desulfurized biomethane/steam mixture fed in via the line 9 at approximately 350° C. is heated to a temperature of approximately 650° C. in the downstream heat exchanger W1. The synthesis gas led off from the heat exchanger W7 is used as a heat carrier, with said gas passing via the line 12 into the heat exchanger W1. This is cooled by the heat exchange process from approximately 950 to approximately 670° C. and is fed via the line 13 to the heat exchanger W2.

After leaving the heat exchanger W1, the methane/steam mixture heated to approximately 650° C. is fed via the line 10 to the primary reformer R2 in which it is converted catalytically to synthesis gas at a reaction temperature of approximately 900° C. Thermal energy is produced additionally in this process because of the excess oxygen in the methane/steam mixture 10 in the primary reformer R2. This energy is produced by an exothermic oxidation of the oxygen contained in the biogas together with hydrogen to initiate the reaction quickly in the catalyst bed.

Dried fermentation substrate 24 is used as a fuel in the processing unit R4 to produce the heat output required for the primary reformer R2. Burning 7800 kg/h of dried fermentation substrate 24 in the auxiliary burner 26 (gas or oil) for start-up and feeding in air 29 produces waste gas at a temperature of 990 to 1030° C. in the combustion chamber B1, generating a heat output of 32 MW. The required reaction heat of 11.23 MW is transferred by radiation to the biomethane or methane. The biomethane or methane is conducted in catalyst pipes in the combustion chamber of the primary reformer R2.

Three main reactions take place in the primary reformer R2 and in the downstream secondary reformer R3 as temperature-dependent equilibrium reactions.

$$H_2 + O_2 \leftrightarrow 2H_2O$$

$$CH_4 + H_2O \leftrightarrow CO + H_2$$

$$CO + H_2O \leftrightarrow CO_2 + H_2$$

The endothermic reaction in the primary reformer R2 requires a heat output of 11.23 MW. Since the oxygen contained in the biogas reacts with hydrogen releasing heat, the temperature of the gas in the catalyst pipes increases spontaneously by about 25° C., providing a suitably hot zone for the endothermic conversion of methane to CO and $H_2$.

Under these conditions about 78% of the methane fed in is catalytically converted to synthesis gas 11 in the primary reformer R2.

The synthesis gas (with a volume of 29996 $Nm^3$/h) exiting the primary reformer R2 via line 11 has the following composition:

| | | |
|---|---|---|
| $CH_4$ | 3.74 | by volume |
| $H_2$ | 45.79 | by volume |
| $H_2O$ | 37.07 | by volume |
| $CO_2$ | 6.70 | by volume |
| CO | 6.63 | by volume |
| $N_2$ | 0.07 | by volume |
| $O_2$ | 0.00 | by volume |
| $SO_2$ | 0.01 | ppm |

1500 $Nm^3$/h of gas containing 92% oxygen by volume and 8% nitrogen by volume and heated in the heat exchanger W7 from 25° C. to 900° C. is subsequently fed to this synthesis gas 11 via the line 25. The synthesis gas exiting the secondary reformer R3 via line 11 and cooling in the process from 1025° C. to 950° C. is used as a heat carrier. The proportion of methane still contained in the synthesis gas 11 is converted with the release of heat to synthesis gas in the secondary reformer R3, with the temperature of the synthesis gas increasing from 900° C. to 1025° C.

The synthesis gas exiting the secondary reformer R3 has the following composition:

| | | |
|---|---|---|
| $CH_4$ | 0.15 | by volume |
| $H_2$ | 48.51 | by volume |
| $H_2O$ | 33.67 | by volume |
| $CO_2$ | 7.17 | by volume |
| CO | 10.03 | by volume |
| $N_2$ | 0.47 | by volume |
| $O_2$ | 0.00 | by volume |
| $SO_2$ | 0.01 | ppm |

Waste heat is recovered repeatedly from the hot synthesis gas to enable the process to be operated in an energy-saving manner, as has already been explained in part above.

The synthesis gas is cooled to a temperature of approximately 950° C. in the heat exchanger W7 by heat emission to the gas containing oxygen. The synthesis gas at a temperature of 950° C. passes to the heat exchanger W1 via the line 12 and is cooled to approximately 670° C. by heat emission to the methane 9. The synthesis gas at a temperature of 670° C. is fed via the line 13 to the steam generator W2 and cooled to 300° C. during steam generation. Heat of 2.78 MW is released in this process which is used to generate 5200 kg/h steam at 20 bar. The steam generated is returned to the steam drum B2.

The synthesis gas at a temperature of approximately 330° C. is subsequently fed via the line 14 to the heat exchanger W3 in which the synthesis gas is cooled at an operating pressure of 15 bar to a temperature 60° C. Hot water at a temperature of 120° C. to 80° C., dependent on the amount of water fed in, is produced thereby via a pressure circuit (pump P3 as well as lines 31, 30, 3), generating 7.3 MW of heat. The amount of heat produced is so high because the major part of the water in the synthesis gas condenses under these conditions. A total of 7688 kg/h condensate accumulates which is pumped back again by the pump P2 via the lines 32, 34 into the steam drum B2 and used to generate steam. The synthesis gas led off from the heat exchanger W3 via the line 15 is further cooled under pressure with cooling water to a temperature of 30° C. in the downstream heat exchanger W4. In this process the cooling water must be cooled with a cooling capacity of 620 KW, with a further 243 kg/h condensate being formed which passes via the line 33 into the line 34. The synthesis gas with a volume of 19,645 $Nm^3$/h pre-dried in this way has the following composition:

| | | |
|---|---|---|
| $CH_4$ | 0.23 | by volume |
| $H_2$ | 72.87 | by volume |
| $H_2O$ | 0.36 | by volume |
| $CO_2$ | 10.78 | by volume |
| CO | 15.06 | by volume |
| $N_2$ | 0.71 | by volume |
| $O_2$ | 0.00 | by volume |
| $SO_2$ | 0.01 | ppm |

This synthesis gas cooled to approximately 30° C. is fed via the line 16 to an amine scrubber K2 in which the carbon dioxide still contained in the synthesis gas is removed and led off via the line 28. After the carbon dioxide has been removed, the synthesis gas exiting the scrubbing column K2 via the line 17 at a rate of 17,550 $Nm^3$/h has the following composition:

| | | |
|---|---|---|
| $CH_4$ | 0.26 | by volume |
| $H_2$ | 81.57 | by volume |
| $H_2O$ | 0.4 | by volume |
| $CO_2$ | 0.12 | by volume |
| CO | 16.86 | by volume |
| $N_2$ | 0.80 | by volume |
| $O_2$ | 0.00 | by volume |
| $SO_2$ | 0.01 | ppm |

The synthesis gas produced in this way can subsequently be further processed (e.g. by drying or separating the parts of hydrogen and carbon monoxide by pressure swing absorption). The synthesis gas produced can also be used to be further synthesized to methanol, ammonia or liquid hydrocarbons.

The hot waste gas drawn off at the head of the primary reformers R2 at a temperature of about 1100° C. is fed via the line 18 to the steam superheater W6, W5. Superheated steam is led off via the line 23 and added to the biomethane or methane. Steam also passes into the steam drum B2.

The connection of the heat exchanger W6 and W5 is represented only symbolically in the functional diagram since both heat exchangers W6 and W5 are interconnected and are not therefore separated by other devices. This is necessary because, owing to different heat transmissions, the heat exchangers must be designed in such a way as to prevent the maximum permissible wall temperatures from being exceeded. The heat exchanger W6 is therefore integrated in the heat exchanger W5 and connected to an economizer that is not shown in the diagram.

The waste gas exiting the steam superheater W6, W5 is at a temperature of approximately 220° C. and is subsequently fed via the line 20 to the gas scrubbing stage K3. The purified waste gas is led off to the surroundings via the line 21.

Condensate is additionally fed to the steam drum B2 (heating via the economizer) via the line 35 and the steam generated is led off via the line 37, said steam can, for example, be used for generating electricity for external use.

The method shown in the example has a very favorable energy balance, as explained briefly below:

After pretreatment in the decanter, fermentation substrate accumulates in the biogas plant BO as a secondary raw material at a rate of 21.2 t/h with a water content of 70%, said substrate having a heating value of 4.1 kW/kg after processing and drying to a residual moisture content of 30%. Using 9.1 t/h of the dried fermentation substrate as a fuel produces a heat output of approximately 37.31 MW.

32 MW of heat output is required to heat the primary reformer R2.

Of that 32 MW, 11.23 MW are consumed in the endothermic conversion as reaction heat for the production of synthesis gas.

18,800 kg/h of steam at 20 bar are produced in the heat exchanger W5 from the waste gas accumulating in the production of synthesis gas, with 14.37 MW being used for heat output.

5200 kg/h steam are generated in the heat exchanger W2 from the synthesis gas fed in via the line 13.

All in all, therefore, 24,000 kg/h of steam are available, of which 13,650 kg/h are required for feeding to the biomethane or methane via the line 23.

10,350 kg/h steam (=7.4 MW) are available for further use.

A heat output of 7.3 MW is obtained from the waste heat recovered from the synthesis gas fed to the heat exchanger W3 via the line 14, therefore making 14.7 MW of heat output available.

Drying the fermentation substrate (hot water 120° C.) and regeneration of the scrubbing solution (hot water 160° C.) consumes 13.9 MW of heat output.

In the case of the regeneration of the scrubbing solution, waste heat at a temperature of 160° C. amounting to 65% of the energy used accumulates from the heating capacity to be used. The waste heat from the regeneration of the scrubbing solution can therefore be used to heat the fermenters (hot water 80° C.) which as a rule need to be heated only at ambient temperatures under 20° C. This therefore leaves a balance of excess thermal energy amounting to 0.8 MW which can be used for other purposes.

In addition, there are still 1.3 t of fermentation substrate available which when burned produce a heat output of 5.31 MW which can possibly be used for generating about 1.0 MW of electricity.

Alternatively, this part of the fermentation substrate can also be used as a fertilizer.

The invention claimed is:

1. A method for producing synthesis gas from biogas, which comprises the steps of:
    removing carbon dioxide and hydrogen sulfide from the biogas by scrubbing, the hydrogen sulfide and the carbon dioxide are removed from the biogas in separate scrubbing stages before a catalytic conversion, the hydrogen sulfide being biologically removed by an addition of at least one of oxygen and an oxidizing agent containing oxygen and one of the oxygen and the oxidizing agent is so dosed that there is oxygen of at least 1.0% by volume in the biogas being methane;
    converting the biogas catalytically to the synthesis gas in a reforming process where the biogas is compressed without dehumidification, heated and mixed with superheated steam and subsequently thermal energy is additionally created during the reforming process by means of an exothermic oxidation of the oxygen contained in the biogas together with hydrogen in a catalyst bed for an endothermic conversion of the methane to the synthesis gas; and
    performing the reforming process as a two stage process, wherein the biogas being compressed to a pressure of 10 to 50 bar and heated to a temperature of 600 to 800° C., is subsequently mixed with oxygen and/or water and, in a first reforming step converted to at least 90% by volume of the synthesis gas at reaction temperatures of 800 to 900° C., wherein a part of required thermal energy is produced by reaction of the oxygen contained in the methane, and a further conversion up to over 99.5% by volume of the synthesis gas takes place in a subsequent second reforming stage with oxygen fed in at reaction temperatures of approximately 1,000° C.

2. The method according to claim 1, which further comprises removing the hydrogen sulfide in a fermenter and in a downstream biological desulfurization stage, wherein for partial desulfurization of the biogas the oxygen and the oxidizing agent containing oxygen are added to the fermenter and residual hydrogen sulfide is removed in the downstream biological desulfurization stage by a further addition of one of the oxygen and the oxidizing agent containing oxygen.

3. The method according to claim 2, which further comprises adding a total amount of the oxygen and/or the oxidizing agent containing oxygen required during the downstream biological desulfurization stage.

4. The method according to claim 1, which further comprises storing the biogas containing the hydrogen sulfide produced in a biogas plant temporarily and a required amount of the oxygen and/or the oxidizing agent containing oxygen is added to the biogas during an interim storage.

5. The method according to claim 1, wherein the biogas still contains at least 0.05% by volume of hydrogen.

6. The method according to claim 1, which further comprises measuring excess oxygen in the biogas and this serves as a control variable for a supply of water and external thermal energy for the reforming process.

7. The method according to claim 1, which further comprises removing the carbon dioxide contained in the biogas and residual amounts of the hydrogen sulfide by means of one of physical scrubbing and chemical scrubbing with a scrubbing solution containing an amine.

8. The method according to claim 1, which further comprises that all constituents of organic sulfur are completely removed before an initiation of the reforming process.

9. The method according to claim 1, wherein the synthesis gas produced during the reforming process and waste gas accumulating in the process each undergo several separate heat recovery stages and thermal energy recovered thereby is used at least partly for generating at least one of steam and hot water.

10. The method according to claim 1, which further comprises producing the superheated steam added to the biogas before the reforming process from condensate accumulating in heat recovery stages.

11. The method according to claim 1, which further comprises using the synthesis gas produced in a second reforming stage for an indirect heating of the methane.

12. The method according to claim 1, which further comprises using fermentation substrate accumulated in a biogas plant after being dried as a fuel to produce a reaction heat for a first reforming stage.

13. The method according to claim 1, which further comprises:
subjecting the synthesis gas to an amine scrubber; and
feeding respective scrubbing solutions from the scrubbing of the biogas and the scrubbing of the synthesis gas to a common regenerator for the scrubbing solution and purified scrubbing solution is circulated in a circuit.

14. The method according to claim 1, which further comprises feeding, gas containing oxygen heated in a heat exchanger to a synthesis gas temperature, to the synthesis gas before being fed into a secondary reformer.

15. The method according to claim 14, which further comprises preparing the gas containing oxygen via a pressure swing adsorption plant.

* * * * *